United States Patent
Dong et al.

(10) Patent No.: US 9,981,903 B2
(45) Date of Patent: May 29, 2018

(54) METHOD FOR PREPARING DI- OR TRICARBOXYLIC ESTERS BY ALKOXYCARBONYLATION OF DIENES HAVING CONJUGATED DOUBLE BONDS

(71) Applicant: EVONIK DEGUSSA GMBH, Essen (DE)

(72) Inventors: Kaiwu Dong, Bo Zhou (CN); Ralf Jackstell, Cuxhaven Altenwalde (DE); Matthias Beller, Ostseebad Nienhagen (DE); Dirk Fridag, Haltern am See (DE); Dieter Hess, Marl (DE); Katrin Marie Dyballa, Recklinghausen (DE); Frank Geilen, Haltern am See (DE); Robert Franke, Marl (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days. days.

(21) Appl. No.: 15/651,105

(22) Filed: Jul. 17, 2017

(65) Prior Publication Data
US 2018/0022687 A1    Jan. 25, 2018

(30) Foreign Application Priority Data
Jul. 19, 2016    (EP) .................................. 16180048

(51) Int. Cl.
*C07C 67/38* (2006.01)
*B01J 27/13* (2006.01)

(52) U.S. Cl.
CPC .............. *C07C 67/38* (2013.01); *B01J 27/13* (2013.01)

(58) Field of Classification Search
CPC ..................................................... C07C 67/38
See application file for complete search history.

(56) References Cited

U.S. PATENT DOCUMENTS

| | | | | |
|---|---|---|---|---|
| 4,792,620 A | * | 12/1988 | Paulik ................. | B01J 31/0231 560/232 |
| 2006/0235241 A1 | | 10/2006 | Drent et al. | |
| 2009/0131630 A1 | * | 5/2009 | Van Broekhoven .... | C07C 51/14 528/335 |
| 2017/0022137 A1 | | 1/2017 | Dong et al. | |
| 2017/0022138 A1 | | 1/2017 | Dong et al. | |
| 2017/0022139 A1 | | 1/2017 | Dong et al. | |
| 2017/0022234 A1 | | 1/2017 | Jennerjahn et al. | |
| 2017/0022235 A1 | | 1/2017 | Dong et al. | |
| 2017/0022236 A1 | | 1/2017 | Dong et al. | |

OTHER PUBLICATIONS

Norskov et al, Nature Chemistry, Towards the Computational Design of Solid Catalysts, 2009, 1, pp. 37-46. (Year: 2009).*
Fang et al, Angewandte Chemie International Edition, Palladium-Catalyzed Alkoxycarbonylation of Conjugated Dienes under Acid-Free Conditions: Atom-Economic Synthesis of b,g-Unsaturated Esters. 2014, 53, pp. 9030-9034.*
European Search Report dated Jan. 11, 2017 for EP 16 18 0048 (1 page).
Fang, X., Li, H., Jackstell, R. and Beller, M. (2014), Palladium-catalyzed alkoxycarbonylation of conjugated diener under acid-free conditions: Atom-economic synthesis of β,γ-unsaturated esters. Angew. Chem. Int. Ed., 53: 9030-9034.
U.S. Appl. No. 15/649,743, filed Jul. 14, 2017, Dong, et al.
U.S. Appl. No. 15/649,759, filed Jul. 14, 2017, Dong, et al.
U.S. Appl. No. 15/649,770, filed Jul. 14, 2017, Dong, et al.
U.S. Appl. No. 15/649,781, filed Jul. 14, 2017, Dong, et al.
U.S. Appl. No. 15/651,042, filed Jul. 17, 2017, Fang, et al.
U.S. Appl. No. 15/651,169, filed Jul. 17, 2017, Dong, et al.
U.S. Appl. No. 15/651,062, filed Jul. 17, 2017, Dong, et al.

* cited by examiner

*Primary Examiner* — Paul A Zucker
(74) *Attorney, Agent, or Firm* — Smith, Gambrell & Russell, LLP

(57) ABSTRACT

The invention relates to a method for preparing di- or tricarboxylic esters by alkoxycarbonylation of dienes having conjugated double bonds. The method includes the steps of initially charging a diene having two conjugated double bonds, adding a phosphine ligand according to formula (I) and a catalyst precursor, adding an alcohol, feeding in CO, and heating the reaction mixture with conversion of the diene to a di- or tricarboxylic ester.

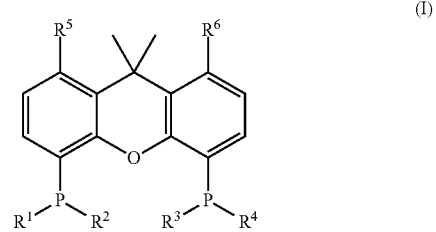

(I)

11 Claims, No Drawings

METHOD FOR PREPARING DI- OR TRICARBOXYLIC ESTERS BY ALKOXYCARBONYLATION OF DIENES HAVING CONJUGATED DOUBLE BONDS

The present invention relates to a novel method for preparing di- or tricarboxylic esters by alkoxycarbonylation of dienes having conjugated double bonds.

Dienes having conjugated double bonds (1,3-dienes), particularly 1,3-butadiene and isoprene, have diverse application in the chemical industry and serve for example as base material for preparing synthetic rubber. A further promising application is the alkoxycarbonylation of 1,3-dienes to give dicarboxylic acids and the corresponding esters.

An alkoxycarbonylation is understood to mean the reaction of ethylenically unsaturated compounds such as dienes with carbon monoxide and alcohols in the presence of a metal or a metal complex and a ligand to give the corresponding esters. The following scheme shows the general reaction equation of the alkoxycarbonylation of an ethylenically unsaturated compound.

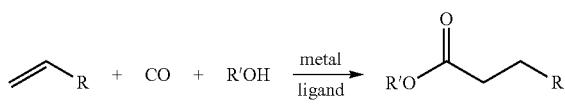

It is known that by application of this method, 1,3-butadiene may be reacted to give dimethyl adipate for example, an important base material for nylon synthesis. The synthesis of dimethyl adipate is accomplished in this case in two steps, wherein 1,3-butadiene is firstly reacted to give the β,γ-unsaturated ester methyl 3-pentenoate, which is subsequently alkoxycarbonylated to give dimethyl adipate [Fang, X., Li, H., Jackstell, R. and Beller, M. (2014), Palladium-catalyzed alkoxycarbonylation of conjugated dienes under acid-free conditions: Atom-economic synthesis of β,γ-unsaturated esters. Angew. Chem. Int. Ed., 53: 9030-9034]. A disadvantage of this reaction, however, is that it is carried out in two steps and in each step a respectively different catalyst complex has to be used. This produces unnecessary waste and causes high costs in the manufacturing process.

Against this background, the object of the present invention is to provide a novel method for preparing di- or tricarboxylic esters, such as dimethyl adipate, with which high yields of the di- or tricarboxylic ester can be attained even in one reaction step.

The object is achieved by a method comprising the method steps of:
a) initially charging a diene having two conjugated double bonds;
b) adding a phosphine ligand and a catalyst precursor selected from palladium dichloride ($PdCl_2$), palladium dibromide ($PdBr_2$), palladium diiodide ($PdI_2$), palladium (II) acetylacetonate [$Pd(acac)_2$], palladium(II) acetate [$Pd(OAc)_2$], bis(dibenzylideneacetone)palladium [$Pd(dba)_2$], bis(acetonitrile)dichloropalladium(II) [$Pd(CH_3CN)_2Cl_2$], palladium (cinnamyl) dichloride [$Pd(cinnamyl)C_2$];
c) adding an alcohol;
d) feeding in CO;
d) heating the reaction mixture, with conversion of the diene to a di- or tricarboxylic ester;
wherein the phosphine ligand is a compound according to formula (I)

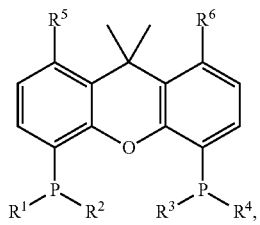

where
$R^1$, $R^2$, $R^3$, $R^4$ are selected from —$(C_1$-$C_{12})$-alkyl, —$(C_6$-$C_{20})$-aryl, —$(C_3$-$C_{12})$-cycloalkyl, —$(C_3$-$C_{12})$-heterocycloalkyl, —$(C_3$-$C_{20})$-heteroaryl;
$R^5$, $R^6$ are selected from —H, —$(C_1$-$C_{12})$-alkyl, —$(C_6$-$C_{20})$-aryl, —$(C_3$-$C_{12})$-cycloalkyl, —$(C_3$-$C_{12})$-heterocycloalkyl, —$(C_3$-$C_{20})$-heteroaryl;
and $R^1$, $R^2$, $R^3$, $R^4$, $R^5$, $R^6$, in the case that these are —$(C_1$-$C_{12})$-alkyl, —$(C_6$-$C_{20})$-aryl, —$(C_3$-$C_{12})$-cycloalkyl, —$(C_3$-$C_{12})$-heterocycloalkyl or —$(C_3$-$C_{20})$-heteroaryl, may each be substituted independently of one another by one or more substituents selected from —$(C_1$-$C_{12})$-alkyl, —$(C_3$-$C_{12})$-cycloalkyl, —$(C_3$-$C_{12})$-heterocycloalkyl, —O—$(C_1$-$C_{12})$-alkyl, —O—$(C_1$-$C_{12})$-alkyl-$(C_6$-$C_{20})$-aryl, —O—$(C_3$-$C_{12})$-cycloalkyl, —S—$(C_1$-$C_{12})$-alkyl, —S—$(C_3$-$C_{12})$-cycloalkyl, —COO—$(C_1$-$C_{12})$-alkyl, —COO—$(C_3$-$C_{12})$-cycloalkyl, —CONH—$(C_1$-$C_{12})$-alkyl, —CONH—$(C_3$-$C_{12})$-cycloalkyl, —CO—$(C_1$-$C_{12})$-alkyl, —CO—$(C_3$-$C_{12})$-cycloalkyl, —N—[$(C_1$-$C_{12})$-alkyl]$_2$, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_3$-$C_{20})$-heteroaryl, —$(C_3$-$C_{20})$-heteroaryl-$(C_1$-$C_{12})$-alkyl, —$(C_3$-$C_{20})$-heteroaryl-O—$(C_1$-$C_{12})$-alkyl, —COOH, —OH, —$SO_3H$, —$NH_2$, halogen.

In this process, process steps a), b), c) and d) can be effected in any desired sequence. Typically, however, the addition of CO is effected after the co-reactants have been initially charged in steps a) to c). Steps d) and e) can be effected simultaneously or successively. In addition, CO can also be fed in two or more steps, in such a way that, for example, a portion of the CO is first fed in, then the mixture is heated, and then a further portion of CO is fed in.

It has been shown, surprisingly, that the combination according to the invention of phosphine ligand and catalyst precursor enables the direct conversion of the diene to the corresponding di- or tricarboxylic ester, wherein only low amounts of β,γ-unsaturated monocarboxylic ester are obtained as by-product. Di- or tricarboxylic esters can thus be prepared by the method according to the invention more simply than with the alkoxycarbonylation methods known from the prior art.

The expression $(C_1$-$C_{12})$-alkyl encompasses straight-chain and branched alkyl groups having 1 to 12 carbon atoms. These are preferably $(C_1$-$C_8)$-alkyl groups, more preferably $(C_1$-$C_6)$-alkyl, most preferably $(C_1$-$C_4)$-alkyl.

Suitable $(C_1$-$C_{12})$-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The elucidations relating to the expression $(C_1-C_{12})$-alkyl also apply in particular to the alkyl groups in —O—$(C_1-C_{12})$-alkyl, —S—$(C_1-C_{12})$-alkyl, —COO—$(C_1-C_{12})$-alkyl, —CONH—$(C_1-C_{12})$-alkyl, —CO—$(C_1-C_{12})$-alkyl and —N—[$(C_1-C_{12})$-alkyl]$_2$.

The expression $(C_3-C_{12})$-cycloalkyl encompasses mono-, bi- or tricyclic hydrocarbyl groups having 3 to 12 carbon atoms. Preferably, these groups are $(C_5-C_{12})$-cycloalkyl.

The $(C_3-C_{12})$-cycloalkyl groups have preferably 3 to 8, more preferably 5 or 6, ring atoms.

Suitable $(C_3-C_{12})$-cycloalkyl groups are especially cyclopropyl, cyclobutyl, cyclopentyl, cyclohexyl, cycloheptyl, cyclooctyl, cyclododecyl, cyclopentadecyl, norbornyl, adamantyl.

The elucidations relating to the expression $(C_3-C_{12})$-cycloalkyl also apply in particular to the cycloalkyl groups in —O—$(C_3-C_{12})$-cycloalkyl, —S—$(C_3-C_{12})$-cycloalkyl, —COO—$(C_3-C_{12})$-cycloalkyl, —CONH—$(C_3-C_{12})$-cycloalkyl, —CO—$(C_3-C_{12})$-cycloalkyl.

The expression $(C_3-C_{12})$-heterocycloalkyl encompasses nonaromatic, saturated or partly unsaturated cycloaliphatic groups having 3 to 12 carbon atoms, where one or more of the ring carbon atoms are replaced by heteroatoms. The $(C_3-C_{12})$-heterocycloalkyl groups have preferably 3 to 8, more preferably 5 or 6, ring atoms and are optionally substituted by aliphatic side chains. In the heterocycloalkyl groups, as opposed to the cycloalkyl groups, one or more of the ring carbon atoms are replaced by heteroatoms or heteroatom-containing groups. The heteroatoms or the heteroatom-containing groups are preferably selected from O, S, N, N($=$O), C($=$O), S($=$O). A $(C_3-C_{12})$-heterocycloalkyl group in the context of this invention is thus also ethylene oxide.

Suitable $(C_3-C_{12})$-heterocycloalkyl groups are especially tetrahydrothiophenyl, tetrahydrofuryl, tetrahydropyranyl and dioxanyl.

The expression $(C_6-C_{20})$-aryl encompasses mono- or polycyclic aromatic hydrocarbyl radicals having 6 to 20 carbon atoms. These are preferably $(C_6-C_{14})$-aryl, more preferably $(C_6-C_{10})$-aryl.

Suitable $(C_6-C_{20})$-aryl groups are especially phenyl, naphthyl, indenyl, fluorenyl, anthracenyl, phenanthrenyl, naphthacenyl, chrysenyl, pyrenyl, coronenyl. Preferred $(C_6-C_{20})$-aryl groups are phenyl, naphthyl and anthracenyl.

The expression $(C_3-C_{20})$-heteroaryl encompasses mono- or polycyclic aromatic hydrocarbyl radicals having 3 to 20 carbon atoms, where one or more of the carbon atoms are replaced by heteroatoms. Preferred heteroatoms are N, O and S. The $(C_3-C_{20})$-heteroaryl groups have 3 to 20, preferably 6 to 14, particularly preferably 6 to 10 ring atoms.

Suitable $(C_3-C_{20})$-heteroaryl groups are especially furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl.

The expression halogen especially encompasses fluorine, chlorine, bromine and iodine. Particular preference is given to fluorine and chlorine.

In one embodiment, the radicals $R^1$, $R^2$, $R^3$, $R^4$, $R^5$, $R^6$, in the case that these are —$(C_1-C_{12})$-alkyl, —$(C_6-C_{20})$-aryl, —$(C_3-C_{12})$-cycloalkyl, —$(C_3-C_{12})$-heterocycloalkyl or —$(C_3-C_{20})$-heteroaryl, may be each substituted independently of one another by one or more substituents selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —SO$_3$H, —NH$_2$, halogen.

In one embodiment, the radicals $R^1$, $R^2$, $R^3$, $R^4$, $R^5$, $R^6$, in the case that these are —$(C_1-C_{12})$-alkyl, —$(C_6-C_{20})$-aryl, —$(C_3-C_{12})$-cycloalkyl, —$(C_3-C_{12})$-heterocycloalkyl or —$(C_3-C_{20})$-heteroaryl, may be each substituted independently of one another by one or more substituents selected from —$(C_1-C_{12})$-alkyl, —$(C_3-C_{12})$-cycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl.

In one embodiment, the radicals $R^1$, $R^2$, $R^3$, $R^4$, $R^5$, $R^6$, if they are —$(C_1-C_{12})$-alkyl, —$(C_6-C_{20})$-aryl, —$(C_3-C_{12})$-cycloalkyl, —$(C_3-C_{12})$-heterocycloalkyl or —$(C_3-C_{20})$-heteroaryl, may be each independently of one another substituted by one or more substituents selected from —$(C_1-C_{12})$-alkyl, —$(C_3-C_{12})$-cycloalkyl, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl.

In one embodiment, the radicals $R^1$, $R^2$, $R^3$, $R^4$, $R^5$, $R^6$, if they are —$(C_1-C_{12})$-alkyl, —$(C_6-C_{20})$-aryl, —$(C_3-C_{12})$-cycloalkyl, —$(C_3-C_{12})$-heterocycloalkyl or —$(C_3-C_{20})$-heteroaryl, may be each independently of one another substituted by one or more substituents selected from —$(C_1-C_{12})$-alkyl, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl.

In one embodiment, the radicals $R^1$, $R^2$, $R^3$, $R^4$, $R^5$, $R^6$ are unsubstituted if they are —$(C_1-C_{12})$-alkyl, —$(C_6-C_{20})$-aryl, —$(C_3-C_{12})$-cycloalkyl, —$(C_3-C_{12})$-heterocycloalkyl or —$(C_3-C_{20})$-heteroaryl.

In a preferred embodiment, $R^1$, $R^2$, $R^3$, $R^4$ are selected from —$(C_1-C_{12})$-alkyl, —$(C_6-C_{20})$-aryl, —$(C_3-C_{12})$-cycloalkyl, —$(C_3-C_{20})$-heteroaryl; particularly preferably from —$(C_1-C_{12})$-alkyl, —$(C_6-C_{20})$-aryl, —$(C_3-C_{20})$-heteroaryl. Most preferably, $R^1$, $R^2$, $R^3$, $R^4$ are in each case —$(C_6-C_{20})$-aryl. In this case, $R^1$, $R^2$, $R^3$, $R^4$ may be substituted as described above. However, $R^1$, $R^2$, $R^3$, $R^4$ are in this case preferably unsubstituted.

In a preferred embodiment, $R^5$, $R^6$ are selected from —H, —$(C_1-C_{12})$-alkyl, —$(C_6-C_{20})$-aryl; particularly preferably from —H, —$(C_1-C_{12})$-alkyl. Most preferably, $R^5$, $R^6$ are each —H. In this case, $R^5$, $R^6$, if they are —$(C_1-C_{12})$-alkyl or —$(C_6-C_{20})$-aryl, are substituted as described above. However, $R^5$, $R^6$ are preferably unsubstituted if they are —$(C_1-C_{12})$-alkyl or —$(C_6-C_{20})$-aryl.

In a preferred embodiment, the phosphine ligand is a compound according to formula (1):

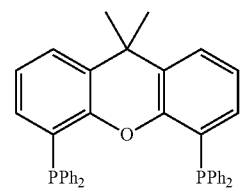

(1)

The diene used as reactant in the method according to the invention comprises at least two conjugated double bonds. The diene may be substituted by one or more alkyl, alkenyl, alkynyl or aryl groups. The diene preferably comprises a total of 4 to 30 carbon atoms, preferably 4 to 22 carbon atoms, most preferably 4 to 12 carbon atoms.

The diene may also comprise more than two double bonds, wherein two of them must be conjugated. In the case that the diene comprises three or more double bonds, it has been shown that it can even be converted directly to a tricarboxylic ester in the reaction according to the invention. Therefore, the reaction according to the invention also comprises the conversion of the diene to a tricarboxylic ester.

The diene may comprise additional functional groups. Preferably, the diene comprises one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, hydroxyl, sulphhydryl, amino, ether, thioether, aryl, heteroaryl or silyl groups and/or halogen substituents. In one embodiment, the diene does not comprise any of these functional groups.

Suitable dienes are in particular 1,3-butadiene, isoprene, 1,3-pentadiene, 2,3-dimethyl-1,3-butadiene, 2,4-dimethyl-1,3-pentadiene, 7-methyl-3-methylene-1,6-octadiene (myrcene) or 2-phenyl-1,3-butadiene.

In one embodiment, the diene is selected from compounds of the formula (II)

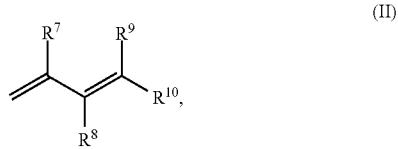

(II)

where $R^7$, $R^8$, $R^9$, $R^{10}$ may each independently be selected from —H, —($C_1$-$C_{12}$)-alkyl and —($C_6$-$C_{20}$)-aryl. Particularly preferably, $R^7$, $R^8$, $R^9$, $R^{10}$ are independently selected from —H, —($C_1$-$C_6$)-alkyl and phenyl. Most preferably, $R^7$, $R^8$, $R^9$, $R^{10}$ are each independently selected from —H, methyl, ethyl and phenyl. The radicals $R^8$, $R^9$ are preferably —H. The radicals $R^8$, $R^9$, $R^{10}$ are particularly preferably —H.

In a particularly preferred embodiment, the diene is selected from 1,3-butadiene, isoprene, 2,3-dimethyl-1,3-butadiene, 2,4-dimethyl-1,3-pentadiene or 2-phenyl-1,3-butadiene. Most preferably, the diene is isoprene.

The alkoxycarbonylation according to the invention is catalysed by a Pd complex. The Pd complex is in this case formed in situ from a compound comprising Pd, and the free phosphine ligand. In this context, the compound comprising Pd is also referred to as catalyst precursor.

The catalyst precursor is selected from palladium dichloride ($PdCl_2$), palladium dibromide ($PdBr_2$), palladium diiodide ($PdI_2$), palladium(II) acetylacetonate [Pd(acac)$_2$], palladium(II) acetate [Pd(OAc)$_2$], bis(dibenzylideneacetone)palladium [Pd(dba)$_2$], bis(acetonitrile)dichloropalladium(II) [Pd(CH$_3$CN)$_2$Cl$_2$], palladium (cinnamyl) dichloride [Pd(cinnamyl)Cl$_2$].

The catalyst precursor is preferably selected from palladium dichloride ($PdCl_2$), palladium dibromide ($PdBr_2$), palladium diiodide ($PdI_2$), palladium(II) acetylacetonate [Pd(acac)$_2$], palladium(II) acetate [Pd(OAc)$_2$], bis(dibenzylideneacetone)palladium [Pd(dba)$_2$].

The catalyst precursor is particularly preferably selected from palladium dichloride ($PdCl_2$), palladium dibromide ($PdBr_2$) and palladium diiodide ($PdI_2$). Most preference is given to palladium dibromide ($PbBr_2$).

The alcohol in method step c) comprises preferably 1 to 30 carbon atoms, more preferably 1 to 22 carbon atoms, especially preferably 1 to 12 carbon atoms. The alcohol may be, for example linear, branched, alicyclic or cyclic. The alcohol may also comprise unsaturated or aromatic groups. The alcohol may comprise one or more hydroxyl groups.

The alcohol may, in addition to the one or more hydroxyl groups, contain further functional groups. Preferably, the alcohol may additionally comprise one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, sulphhydryl, amino, ether, thioether or silyl groups and/or halogen substituents.

In one embodiment, the alcohol does not comprise any further functional groups except for hydroxyl groups.

In one embodiment, the alcohol comprises only one hydroxyl group.

Suitable alcohols are, for example, alkanols or cycloalkanols, particularly methanol, ethanol, 1-propanol, isopropanol, n-butanol, isobutanol, sec-butanol, tert-butanol, 1-pentanol, 2-pentanol, 3-pentanol, 1-hexanol, cyclohexanol, 2-ethylhexanol, isononanol, 2-propylheptanol.

Suitable alcohols are also aryl-substituted alkanols such as, e.g. benzyl alcohol, 1-phenylethanol or 2-phenylethanol.

Suitable alcohols having more than one hydroxyl group are, for example, cyclohexane-1,2-diol, 1,2-ethanediol, 1,3-propanediol, glycerol, 1,2,4-butanetriol, 2-hydroxymethyl-1,3-propanediol, 1,2,6-trihydroxyhexane, pentaerythritol, 1,1,1-tri(hydroxymethyl)ethane, catechol, resorcinol and hydroxyhydroquinone.

Suitable alcohols are also sucrose, fructose, mannose, sorbose, galactose and glucose.

In one embodiment, the alcohol in method step c) is selected from methanol, ethanol, 1-propanol, isopropanol, n-butanol, isobutanol, sec-butanol, tert-butanol, 1-pentanol, 2-pentanol, 3-pentanol, 1-hexanol, cyclohexanol, 2-ethylhexanol, isononanol, 2-propylheptanol, benzyl alcohol, 1-phenylethanol or 2-phenylethanol.

The alcohol in method step c) is preferably selected from methanol, ethanol, 1-propanol, isopropanol, n-butanol, isobutanol, sec-butanol, tert-butanol or 2-phenylethanol.

The alcohol in method step c) is particularly preferably selected from methanol, ethanol, isopropanol, n-butanol or 2-phenylethanol.

Most preferably, the alcohol in method step c) is methanol.

In one variant of the method, the alcohol in method step c) is used in excess.

In one variant of the method, the alcohol in method step c) is used simultaneously as solvent.

In one variant of the method, a further solvent is used, selected from, for example: toluene, xylene, hexane, heptane, tetrahydrofuran (THF) or methylene chloride ($CH_2Cl_2$). Particularly preferred solvents are toluene and xylene (particularly p-xylene).

CO is fed in step d) preferably at a partial CO pressure between 0.1 and 10 MPa (1 to 100 bar), preferably between 1 and 8 MPa (10 to 80 bar), particularly preferably between 3 and 6 MPa (30 to 60 bar), most preferably between 3.5 and 4.5 MPa (35 to 45 bar).

The reaction mixture is heated in step e) of the method according to the invention preferably to a temperature between 10° C. and 180° C., more preferably between 20 and 160° C., particularly preferably between 80 and 160° C., most preferably between 130 and 150° C., in order to convert the diene to a di- or tricarboxylic ester.

The molar ratio of the diene initially charged in step a) to the alcohol added in step c) is preferably between 1:1 and 1:20, more preferably 1:2 to 1:10, especially preferably 1:3 to 1:4.

The mass ratio of Pd to the diene initially charged in step a) is preferably between 0.001% and 0.5% by weight, more preferably between 0.01% and 0.1% by weight, especially preferably between 0.01% and 0.05% by weight.

The molar amount of Pd, based on the molar amount of the diene initially charged in step a), is preferably between 0.1 and 10 mol %, preferably 0.5 to 5 mol %, particularly preferably 0.8 to 2 mol %.

The molar ratio of the phosphine ligand to Pd is preferably between 0.1:1 and 400:1, more preferably between 0.5:1 and 400:1, especially preferably between 1:1 and 100:1, most preferably between 2:1 and 50:1.

Preferably, the method is conducted with addition of an acid. In one variant, the method therefore additionally comprises step c'): adding an acid to the reaction mixture. This may preferably be a Brønsted or Lewis acid.

Suitable Brønsted acids preferably have an acid strength of $pK_a \leq 5$, more preferably an acid strength of $pK_a \leq 3$. The reported acid strength $pK_a$ is based on the $pK_a$ determined under standard conditions (25° C., 1.01325 bar). In the case of a polyprotic acid, the acid strength pKa in the context of this invention relates to the pKa of the first protolysis step.

Preferably, the acid is not a carboxylic acid.

Suitable Brønsted acids are, for example, perchloric acid, sulphuric acid, phosphoric acid, methylphosphonic acid and sulphonic acids. Preferably, the acid is sulphuric acid or a sulphonic acid. Suitable sulphonic acids are, for example, methanesulphonic acid, trifluoromethanesulphonic acid, tert-butanesulphonic acid, p-toluenesulphonic acid (PTSA), 2-hydroxypropane-2-sulphonic acid, 2,4,6-trimethylbenzenesulphonic acid and dodecylsulphonic acid. Particularly preferred acids are sulphuric acid, methanesulphonic acid, trifluoromethanesulphonic acid and p-toluenesulphonic acid.

A Lewis acid used may, for example, be aluminium triflate.

In one embodiment, the amount of acid added in step c') is 0.3 to 40 mol %, preferably 0.4 to 15 mol %, particularly preferably 0.5 to 5 mol %, most preferably 0.6 to 3 mol %, based on the molar amount of the diene initially charged in step a).

EXAMPLES

The examples which follow illustrate the invention.
General Procedure Specifications Unless stated otherwise, relative molar amounts in mol % refer to the molar amount of olefin (substrate).

All reaction products were isolated from the reaction mixture by column chromatography over silica gel 60, 0.063-0.2 mm, 70-230 mesh from Merck.

Gel chromatography analyses (GC analyses) were carried out using an instrument of the Agilent GC 7890A type from Agilent using an HP5 column (polydimethylsiloxane with 5% phenyl groups, 30 m, 0.32 mm i.d., 0.25 µm film thickness). Temperature program: 35° C., 10 min.; 10° C./min to 285° C., 5 min.; injection volume 1 µl with a split of 50:1. The retention times of the purified products are specified in the following table:

| Product | Retention time (min) |
|---|---|
| MeOOC–\–COOMe | 22.0 |
| EtOOC–\–COOEt | 23.6 |
| $^i$PrOOC–\–COO$^i$Pr | 24.3 |
| $^n$BuOOC–\–COO$^n$Bu | 27.4 |
| RO–C(O)–\–C(O)–OR, R = CH$_2$CH$_2$C$_6$H$_5$ | 35.3 |
| $^n$BuOOC–\–COO$^n$Bu | 28.0 |
| $^n$BuOOC–\–COO$^n$Bu | 28.5 |
| $^n$BuOOC–\–(Ph)–COO$^n$Bu | 31.6 |
| $^n$BuOOC–\–(branched)–COO$^n$Bu | 35.1 |

Alkoxycarbonylation of Isoprene with n-Butanol Using Different Ligands

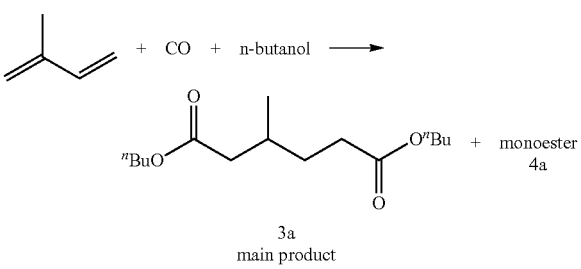

A 4 ml sample vial was charged with PdBr$_2$ (2.64 mg, 1.0 mol %), PTSA (9.5 mg, 5.0 mol %), the respective ligand (2.0 mol %) and a magnetic stirrer bar. The vial was sealed with a septum (PTFE-coated styrene-butadiene rubber) and a phenol resin cap. Gas exchange between sample vial and environment was enabled by means of a cannula pierced through the septum. The sample vial was purged three times with argon. Para-xylene (2.0 ml), isoprene (100 μl, 1.0 mmol) and n-butanol (274 μl, 3.0 mmol) were injected into the sample vial by means of a syringe. The sample vial was placed on a metal plate and this was transferred under an argon atmosphere into a 300 ml autoclave of the 4560 type from Parr Instruments. After the autoclave had been purged three times with CO, the CO pressure was adjusted to 40 bar at room temperature. The reaction ran for 48 hours at 120° C. After completion of the reaction, the autoclave was cooled to room temperature and carefully decompressed. Isooctane (100 μl) was added as internal GO standard. The yield of dicarboxylic ester (3a) and monocarboxylic ester (4a) was determined by GC. The results are compiled in the following table. The ligands used in each case are commercially available compounds.

| Example | Ligand | Yield 3a | Yield 4a |
|---|---|---|---|
| 1 | No ligand | — | 68% |
| 2* | (ligand 1) | 89% | 11% |
| 2 | (comparative example) | 0 | 42% |
| 3 | (comparative example) | 0 | 42% |
| 4 | (comparative example) | 0 | 0 |

*inventive example

As this experiment shows, ligand 1, used according to the invention as sole ligand investigated, is capable of converting isoprene in one step to a dicarboxylic acid. With ligands 2 to 4 described in the prior art in the context of alkoxycarbonylation of isoprene (cf. X. Fang et al, Angew. Chem. Int. Ed., 2014, 53, 9030-9034) at best monoesters but no dicarboxylic esters are obtained.

Alkoxycarbonylation of Isoprene with n-Butanol Using Different Catalyst Precursors A 4 ml sample vial was charged with 1.0 mol % or 0.5 mol % of the respective catalyst precursor, PTSA (9.5 mg, 5.0 mol %), ligand 1 (11.6 mg, 2.0 mmol %) and a magnetic stirrer bar. The vial was sealed with a septum (PTFE-coated styrene-butadiene rubber) and a phenol resin cap. Gas exchange between sample vial and environment was enabled by means of a cannula pierced through the septum. The sample vial was purged three times with argon. Para-xylene (2.0 ml), isoprene (100 μl, 1.0 mmol) and n-butanol (274 μl, 3.0 mmol) were injected into the sample vial by means of a syringe. The sample vial was placed on a metal plate and this was transferred under an argon atmosphere into a 300 ml autoclave of the 4560 type from Parr Instruments. After the autoclave had been purged three times with CO, the CO pressure was adjusted to 40 bar at room temperature. The reaction ran for 48 hours at 140° C. After completion of the reaction, the autoclave was cooled to room temperature and carefully decompressed. Isooctane (100 μl) was added as internal GC standard. The yield of dicarboxylic ester (3a) and monoester (4a) was determined by GC. The results are compiled in the following table.

| Example | Catalyst precursor | Yield 3a | Yield 4a |
|---|---|---|---|
| 1 | 1.0 mol % $PdCl_2$ | 71% | 26% |
| 2 | 1.0 mol % $PdBr_2$ | 89% | 11% |
| 3 | 1.0 mol % $PdI_2$ | 67% | 19% |
| 4 | 1.0 mol % $Pd(OAc)_2$ | 41% | 32% |
| 5 | 1.0 mol % $Pd(acac)_2$ | 44% | 27% |
| 6 | 0.5 mol % $Pd_2(dba)_3$ | 24% | 52% |

This experiment shows that direct conversion of isoprene to dicarboxylic ester can be achieved with different catalyst precursors used in accordance with the invention. The best results are achieved here using $PdCl_2$, $PdBr_2$, $PdI_2$.

Alkoxycarbonylation of Different Dienes with Different Alcohols

A 4 ml sample vial was charged with $PdBr_2$, PTSA, ligand 1 in the amount specified and a magnetic stirrer bar. The vial was sealed with a septum (PTFE-coated styrene-butadiene rubber) and a phenol resin cap. Gas exchange between sample vial and environment was enabled by means of a cannula pierced through the septum. The sample vial was purged three times with argon. Para-xylene (2.0 ml), 1.0 mmol of diene and 3.0 mmol of alcohol were injected into the sample vial by means of a syringe. The sample vial was placed on a metal plate and this was transferred under an argon atmosphere into a 300 ml autoclave of the 4560 type from Parr Instruments. After the autoclave had been purged three times with CO, the CO pressure was adjusted to 40 bar at room temperature. The reaction ran for 48 or 96 hours at 140° C. After completion of the reaction, the autoclave was cooled to room temperature and carefully decompressed. Isooctane (100 μl) was added as internal GC standard. The yield of the main product was determined by means of GC analysis. The results are compiled in the following table.

| Example[1] | Diene | Alcohol | Main product | Yield |
|---|---|---|---|---|
| 1 | Isoprene | Methanol | MeOOC∼∼∼COOMe | 76% |
| 2 | Isoprene | Ethanol | EtOOC∼∼∼COOEt | 82% |
| 3 | Isoprene | Isopropanol | $^i$PrOOC∼∼∼COO$^i$Pr | 70% |
| 4 | Isoprene | n-Butanol | $^n$BuOOC∼∼∼COO$^n$Bu | 94% |
| 5 | Isoprene | 2-Phenylethanol | RO-C(O)-CH2-CH(CH3)-CH2-CH2-C(O)-OR, R = CH$_2$CH$_2$C$_6$H$_5$ | 94% |
| 6 | (2,3-dimethylbutadiene) | n-Butanol | $^n$BuOOC∼∼∼COO$^n$Bu | 79% |
| 7 | (2,4-hexadiene) | n-Butanol | $^n$BuOOC∼∼∼COO$^n$Bu | 99% |
| 8 | Ph-diene | n-Butanol | $^n$BuOOC∼∼(Ph)∼COO$^n$Bu | 30% |
| 9 | myrcene | n-Butanol | 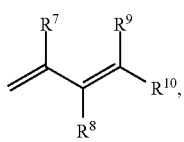 | 37% |

[1]examples 1 to 5, 7 and 8: 1.0 mol % PdBr$_2$, 2.0 mol % ligand 1, 5.0 mol % PTSA, 48 h; examples 6 and 9: 2.0 mol % PdBr$_2$, 4.0 mol % ligand 1, 10.0 mol % PTSA, 96 h.

The examples described above show that 1,3-dienes, isoprene for example, may be converted directly to di- or tricarboxylic esters with the method according to the invention. This is an advantage compared to the two-step method for preparing dicarboxylic esters in the prior art. Use of different alcohols was also shown to be successful.

The invention claimed is:

1. A method for preparing di- or tricarboxylic esters in a reaction mixture, comprising the method steps of:

a) initially charging a diene having two conjugated double bonds, wherein the diene is selected from compounds of the formula (II)

$$\underset{R^8}{\overset{R^7}{\diagup}}=\underset{}{\overset{R^9}{\diagdown}}R^{10},\quad (II)$$

where $R^7$, $R^8$, $R^9$, $R^{10}$ may each independently be selected from —H, —(C$_1$-C$_{12}$)-alkyl, or —(C$_6$-C$_{20}$)-aryl;

b) adding a phosphine ligand and a catalyst precursor selected from palladium dichloride, palladium dibromide, palladium diiodide, palladium(II) acetylacetonate, palladium(II) acetate, bis(dibenzylideneacetone) palladium, bis(acetonitrile)dichloropalladium(II), or palladium (cinnamyl) dichloride;

c) adding an alcohol;

d) feeding in CO;
e) heating the reaction mixture, with conversion of the diene to a di- or tricarboxylic ester;

wherein the phosphine ligand is a compound according to formula (I)

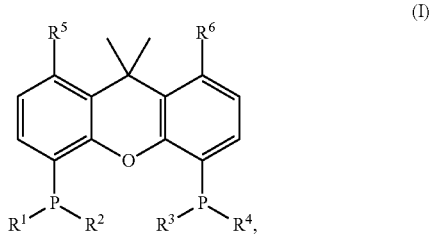

where $R^1$, $R^2$, $R^3$, $R^4$ are selected from —($C_1$-$C_{12}$)-alkyl, —($C_6$-$C_{20}$)-aryl, —($C_3$-$C_{12}$)-cycloalkyl, —($C_3$-$C_{12}$)-heterocycloalkyl, or —($C_3$-$C_{20}$)-heteroaryl;

$R^5$, $R^6$ are selected from —H, —($C_1$-$C_{12}$)-alkyl, —($C_6$-$C_{20}$)-aryl, —($C_3$-$C_{12}$)-cycloalkyl, —($C_3$-$C_{12}$)-heterocycloalkyl, or —($C_3$-$C_{20}$)-heteroaryl;

and $R^1$, $R^2$, $R^3$, $R^4$, $R^5$, $R^6$, in the case that these are —($C_1$-$C_{12}$)-alkyl, —($C_6$-$C_{20}$)-aryl, —($C_3$-$C_{12}$)-cycloalkyl, —($C_3$-$C_{12}$)-heterocycloalkyl or —($C_3$-$C_{20}$)-heteroaryl, may be each substituted independently of one another by one or more substituents selected from —($C_1$-$C_{12}$)-alkyl, —($C_3$-$C_{12}$)-cycloalkyl, —($C_3$-$C_{12}$)-heterocycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —S—($C_1$-$C_{12}$)-alkyl, —S—($C_3$-$C_{12}$)-cycloalkyl, —COO—($C_1$-$C_{12}$)-alkyl, —COO—($C_3$-$C_{12}$)-cycloalkyl, —CONH—($C_1$-$C_{12}$)-alkyl, —CONH—($C_3$-$C_{12}$)-cycloalkyl, —CO—($C_1$-$C_{12}$)-alkyl, —CO—($C_3$-$C_{12}$)-cycloalkyl, —N—[($C_1$-$C_{12}$)-alkyl]$_2$, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_3$-$C_{20}$)-heteroaryl, —($C_3$-$C_{20}$)-heteroaryl-($C_1$-$C_{12}$)-alkyl, —($C_3$-$C_{20}$)-heteroaryl-O—($C_1$-$C_{12}$)-alkyl, —COOH, —OH, —SO$_3$H, —NH$_2$, or halogen, and wherein steps a), b), c), and d) may be effected in any sequence.

2. The method according to claim 1,
where $R^1$, $R^2$, $R^3$, $R^4$ are selected from —($C_1$-$C_{12}$)-alkyl, —($C_6$-$C_{20}$)-aryl, or ($C_3$-$C_{20}$)-heteroaryl.

3. The method according to claim 1,
where $R^5$, $R^6$ are selected from —H or —($C_1$-$C_{12}$)-alkyl.

4. The method according to claim 1,
where $R^1$, $R^2$, $R^3$, $R^4$ are each —($C_6$-$C_{20}$)-aryl and $R^5$, $R^6$ are each selected from —H or —($C_1$-$C_{12}$)-alkyl.

5. The method according to claim 1,
wherein the diene has 4 to 30 carbon atoms.

6. The method according to claim 1,
wherein the catalyst precursor is selected from palladium dichloride, palladium dibromide, palladium diiodide, palladium(II) acetylacetonate, palladium(II) acetate, or bis(dibenzylideneacetone)palladium.

7. The method according to claim 1,
wherein the catalyst precursor is selected from palladium dichloride, palladium dibromide, or palladium diiodide.

8. The method according to claim 1,
wherein the alcohol in method step c) has 1 to 12 carbon atoms.

9. The method according to claim 1,
wherein the alcohol in method step c) is selected from methanol, ethanol, 1-propanol, isopropanol, n-butanol, isobutanol, sec-butanol, tert-butanol, 1-pentanol, 2-pentanol, 3-pentanol, 1-hexanol, cyclohexanol, 2-ethylhexanol, isononanol, 2-propylheptanol, benzyl alcohol, 1-phenylethanol or 2-phenylethanol.

10. The method according to claim 1,
wherein the alcohol in method step c) is selected from methanol, ethanol, isopropanol, n-butanol or 2-phenylethanol.

11. The method of claim 1, wherein $R^7$, $R^8$, $R^9$, $R^{10}$ may each independently be selected from —H, —($C_1$-$C_6$)-alkyl, or phenyl.

* * * * *